United States Patent
Slik et al.

(10) Patent No.: US 7,925,759 B2
(45) Date of Patent: Apr. 12, 2011

(54) METHOD AND APPARATUS FOR TRANSMISSION AND STORAGE OF DIGITAL MEDICAL DATA

(75) Inventors: David Slik, Burnaby (CA); Tym Altman, Vancouver (CA); Mohammad Kermani, Vancouver (CA); Keith Ma, Richmond (CA); Michael Montour, Vancouver (CA); Walter Proseilo, Calgary (CA); Oliver Seiler, New Westminster (CA)

(73) Assignee: NetApp, Sunnyvale, CA (US)

( * ) Notice: Subject to any disclaimer, the term of this patent is extended or adjusted under 35 U.S.C. 154(b) by 0 days.

(21) Appl. No.: 12/216,282

(22) Filed: Jul. 2, 2008

(65) Prior Publication Data

US 2009/0089303 A1   Apr. 2, 2009

Related U.S. Application Data

(63) Continuation of application No. 10/341,360, filed on Jan. 14, 2003, now Pat. No. 7,624,158.

(51) Int. Cl.
    *G06F 15/173* (2006.01)
(52) U.S. Cl. .............. 709/226; 709/238; 709/217
(58) Field of Classification Search ............ 709/217, 709/226, 238
    See application file for complete search history.

(56) References Cited

U.S. PATENT DOCUMENTS

| | | | | |
|---|---|---|---|---|
| 4,893,270 A | 1/1990 | Beck et al. | | 364/900 |
| 5,146,439 A | 9/1992 | Jachmann et al. | | 369/25 |
| 5,276,871 A | 1/1994 | Howarth | | 395/600 |
| 5,301,105 A | 4/1994 | Cummings, Jr. | | 364/401 |
| 5,319,543 A | 6/1994 | Wilhelm | | 364/401 |
| 5,586,262 A | 12/1996 | Komatsu et al. | | 395/200.02 |
| 5,627,961 A | 5/1997 | Sharman | | 395/182.04 |
| 5,806,075 A | 9/1998 | Jain et al. | | 707/201 |
| 5,815,649 A | 9/1998 | Utter et al. | | 395/112.04 |
| 5,851,186 A | 12/1998 | Wood et al. | | 600/437 |
| 5,857,967 A | 1/1999 | Frid et al. | | 600/301 |
| 5,864,851 A | 1/1999 | Breitbart et al. | | 707/8 |
| 5,867,821 A | 2/1999 | Ballantyne et al. | | 705/2 |
| 5,899,998 A | 5/1999 | McGauley et al. | | 707/104 |
| 5,903,889 A | 5/1999 | de la Huerga et al. | | 707/3 |
| 5,964,700 A | 10/1999 | Tallman et al. | | 600/300 |
| 5,996,089 A | 11/1999 | Mann et al. | | 714/6 |
| 6,018,713 A | 1/2000 | Coli et al. | | 705/2 |
| 6,195,760 B1 | 2/2001 | Chung et al. | | 714/4 |
| 6,216,173 B1 | 4/2001 | Jones et al. | | 709/302 |
| 6,260,021 B1 | 7/2001 | Wong et al. | | 705/2 |
| 6,263,330 B1 | 7/2001 | Bessette | | 707/4 |
| 6,289,115 B1 | 9/2001 | Takeo | | 382/130 |
| 6,292,905 B1 | 9/2001 | Wallach et al. | | 714/4 |
| 6,295,558 B1 | 9/2001 | Davis et al. | | 709/224 |

(Continued)

*Primary Examiner* — Salad Abdullahi
(74) *Attorney, Agent, or Firm* — Roylance, Abrams, Berdo & Goodman, LLP

(57) ABSTRACT

System for decentralized storage and rapid retrieval of medical data among geographically separate locations, connected by data paths of limited bandwidth, which optimizes transmission therebetween. Medical data is separated into bulk content and metadata. Metadata is transmitted to all locations. Bulk content is copied to selected locations based on desired duplication, available storage, distance, transmission cost, data path bandwidth or utilization, likelihood of retrieval calculated from the metadata, requests to use or prior usage of content or information from a system that manages the content. Transmission rate is limited and bulk content is queued for transmission based on priority calculated from metadata, from requests to use content or information from a system that manages the content. Optimal locations for bulk content are recalculated based on requests to use content, new patient appointments, data path or equipment failures. Copies are made or deleted. Distributed lists of locations for content are updated.

20 Claims, 4 Drawing Sheets

U.S. PATENT DOCUMENTS

| | | |
|---|---|---|
| 6,304,788 B1 | 10/2001 | Eady et al. .................... 700/86 |
| 6,324,586 B1 | 11/2001 | Johnson ........................ 709/248 |
| 6,338,092 B1 | 1/2002 | Chao et al. ................... 709/236 |
| 6,350,239 B1 | 2/2002 | Ohad et al. ................... 600/437 |
| 6,351,547 B1 | 2/2002 | Johnson et al. ............... 382/128 |
| 6,366,917 B1 | 4/2002 | St. John Herbert, III ..... 707/100 |
| 6,374,336 B1 | 4/2002 | Peters et al. ................. 711/167 |
| 6,393,485 B1 | 5/2002 | Chao et al. ................... 709/231 |
| 6,415,373 B1 | 7/2002 | Peters et al. ................. 711/167 |
| 6,418,475 B1 | 7/2002 | Fuchs ............................ 709/238 |
| 6,608,628 B1 | 8/2003 | Ross et al. .................... 345/619 |
| 6,678,703 B2 | 1/2004 | Rothschild et al. ........... 707/201 |
| 6,725,274 B1 | 4/2004 | Slik ............................... 709/231 |
| 6,856,414 B1 | 2/2005 | Haneda et al. ............... 358/1.15 |
| 6,933,943 B2 | 8/2005 | Alcorn .......................... 345/506 |
| 6,983,464 B1 | 1/2006 | Bhattacharya et al. ........ 719/318 |
| 2001/0034795 A1* | 10/2001 | Moulton et al. ............... 709/244 |
| 2002/0010670 A1 | 1/2002 | Mosler et al. .................. 705/37 |
| 2002/0028007 A1 | 3/2002 | Gendron et al. .............. 382/128 |
| 2002/0188664 A1 | 12/2002 | Hultgren et al. .............. 705/203 |
| 2003/0005464 A1* | 1/2003 | Gropper et al. ............... 725/115 |
| 2003/0041095 A1 | 2/2003 | Konda et al. .................. 709/201 |
| 2003/0046270 A1* | 3/2003 | Leung et al. ...................... 707/1 |
| 2003/0105389 A1 | 6/2003 | Noonan et al. ................ 600/300 |
| 2003/0115084 A1 | 6/2003 | Gage ................................. 705/3 |
| 2004/0034550 A1 | 2/2004 | Menschik et al. ................ 705/3 |
| 2004/0059604 A1 | 3/2004 | Zaleski ............................. 705/2 |
| 2005/0203867 A1 | 9/2005 | Judd et al. ........................ 707/1 |
| 2005/0240445 A1 | 10/2005 | Sutherland et al. .............. 705/3 |
| 2005/0251012 A1 | 11/2005 | Judd et al. .................... 600/407 |

* cited by examiner

Data Storage

Data Retrieval

METHOD AND APPARATUS FOR TRANSMISSION AND STORAGE OF DIGITAL MEDICAL DATA

This application is a continuation of U.S. patent application Ser. No. 10/341,360, filed Jan. 14, 2003 now U.S. Pat. No. 7,624,158.

CROSS-REFERENCE TO RELATED APPLICATIONS

Related subject matter is disclosed and claimed in U.S. patent application Ser. No. 09/493,087, filed by David Slik on Jan. 28, 2000 (not issued as U.S. Pat. No. 7,028,071); and in U.S. patent application Ser. No. 09/537,419, filed by David Slik on Mar. 29, 2000 (now issued as U.S. Pat. No. 6,725,274); all of said applications being expressly incorporated herein by reference.

FIELD OF THE INVENTION

This invention relates to the transmission and storage of digital medical data (e.g., medical imagery) to geographically separate locations connected by data paths of limited bandwidth.

BACKGROUND OF THE INVENTION

Very large volumes of medical data for each patient can result from techniques such as digitizing x-ray film, computed radiology (CR), computed tomography (CT), magnetic resonance imaging (MRI), positron emission tomography (PET), ultrasound, digital fluorography, digital angiography and video capture of diagnostic and surgical procedures. Such large volumes present a challenge when produced and used at geographically separate locations such as separate hospitals or clinics that are connected by data paths of limited bandwidth.

Existing medical data management systems are generally implemented as an image archiving system at a single location, often with multiple workstations connected to a server, or group of servers, all connected with a high-speed Local Area Network (LAN).

Such prior-art systems have been extended to geographically separate locations, however, the issue of data path bandwidth and transmission cost between locations is generally overlooked, raising the operating costs. The cost of the data paths can be a complex function. For example, some carriers can charge only for the provisioning of a certain bandwidth with no charge for usage, while others can charge for all bandwidth usage or can charge for usage above a specified limit. Furthermore, overloading a data path can, in some cases, cause data to be discarded along the way, requiring retransmission and resulting in a loss of efficiency. In addition, such systems generally store at least some information only at a central location, making the system vulnerable to failure of the central server and data paths to it. This risk many be reduced somewhat by duplicating the central server and data paths, however, this is an expensive alternative.

A need therefore exists for a medical data management system that allow users to economically and rapidly retrieve data at their location while minimizing the cost of the data paths.

A need also exists for a medical data management system that allows capacity to be incrementally expanded to distribute the costs of the equipment over time as usage grows.

A need further exists for a medical data management system that provides reliable operation and no loss of medical data when at least some of the data paths between locations fail, or when at least some of the equipment fails.

A need exists for a medical data management system that provides a degree of privacy for the medical data, ensuring that it is encrypted before transmission or long-term storage.

A need also exists for a medical data management system that allows users to rapidly determine what data is available, where it is located and when it can be transmitted to a given location.

The above-described, desired medical data management system should not be confused with an Electronic Patient Records (EPR) system or Hospital Information System (HIS). Such conventional systems store day-to-day patient records and billing information that is, in general, manually entered and thus small in volume. However, it can be desirable to connect the invention to such an EPR/HIS system in order to obtain information about upcoming patient appointments or other uses of the patient's data, to store audit information related to privacy or to provide notification that data has arrived at a given, or any, location.

SUMMARY OF THE INVENTION

It is an object of the present invention to economically allow users to rapidly retrieve data at their location while minimizing the cost of the data paths.

It is also an object of the present invention to allow capacity to be incrementally expanded; that is, to spread the costs of the equipment over time as usage grows.

It is also an object of the present invention to provide reliable operation and no loss of medical data when at least some of the data paths between locations fail and when at least some of the equipment fails.

It is also an object of the present invention to provide a degree of privacy for the medical data, ensuring that it is encrypted before transmission or long-term storage.

It is also an object of the present invention to allow users to rapidly determine what data is available, where it is located and when it can be transmitted to a given location.

According to the present invention there is provided a method and apparatus for reliable, private, decentralized storage and rapid retrieval of medical data amongst geographically separate locations, connected by data paths of limited bandwidth, which optimizes the transmission between the locations.

A system incorporating the method and apparatus of the present invention is completely distributed and carefully manages the transmission between its locations. The capital cost of its equipment is distributed among its locations based on usage rather than centralized, which can be an advantage to some purchasers.

In accordance with an embodiment of the present invention, an apparatus is provided for distributing medical data between geographically separate locations connected by optical, wired or radio frequency data paths of limited bandwidth. The apparatus is employed at a first one of the locations and comprises: (1) a processing device; (2) a memory device coupled to said processing device; and (3) at least one network interface connected to at least one of said data paths and in communication with said processing device. The processing device is programmable to separate said medical data provided to its corresponding said location into bulk content and metadata, to associate said bulk content with a content identifier, to transmit via said at least one network interface said bulk content to at least one of the other said locations for storage, to extend said metadata to comprise said content identifier and a list of all of said locations where said bulk content has been transmitted for storage, and to transmit via said at least one network interface said extended metadata to at least one of said locations for storage.

In accordance with an embodiment of the present invention, a method is provided for transmission of digital medical data between at least two geographically separate locations connected by data paths of limited bandwidth The method comprises the steps of: (1) separating said medical data arriving at one of said locations into at least bulk content and metadata; (2) associating said bulk content with a content identifier; (3) transmitting said bulk content to at least one other of said locations and storing it; (4) extending said metadata to comprise said content identifier and a list of all of said locations where said bulk content has been and stored; and (5) transmitting said extended metadata to at least some of said locations and storing it.

In accordance with an aspect of the present invention, new medical data presented to the system via a Local Area Network (LAN) at one location is converted into a standard format, if required, and separated into bulk content and a relatively small amount of metadata that describes the content. If not already present in the metadata, the bulk content is assigned a content identifier and the identifier is added to the metadata. The bulk content and the metadata can be encrypted for privacy.

In accordance with another aspect of the present invention, the optimal locations to which to copy the bulk content are calculated based on the desired degree of content duplication, available storage at each location, geographic distance to each location, transmission cost to each location, data path bandwidth to each location, current utilization of the data paths to each location, processor utilization at each location or the likelihood of retrieval at each location calculated from information contained in the metadata, from requests to use or prior usage of the bulk content or from information obtained from an Electronic Patient Records (EPR) system or Hospital Information System (HIS) that manages patient's appointments or other future uses of the bulk content.

In accordance with yet another aspect of the present invention, a congestion management method is used to control the rate of transmission to avoid overloading the data path by requiring transmissions to be queued. In one embodiment, transmissions of the bulk content to the optimal locations are queued based on a priority calculated from information contained in the associated metadata, from requests to use the bulk content or from information obtained from an EPR or HIS system that manages patient's appointments or other future uses of the bulk content.

In accordance with another aspect of the present invention, as the bulk content is copied to the optimal locations, a list of identifiers of all locations where the bulk content has been stored is created. The list is added to the metadata and the metadata is transmitted, generally to all locations, using a synchronization method.

In accordance with yet another aspect of the present invention, over time, the optimal locations for storage of the bulk content are recalculated as events such as requests to use the bulk content, new appointments, data path failures or equipment failures occur. As dictated by the calculation, additional copies are made by transmitting content with a calculated priority, or copies are deleted. When such changes are made, the distributed lists of locations for the content are updated.

In accordance with still yet another aspect of the present invention, when data is to be obtained by a user, the metadata at the user's location or a nearby location is searched to obtain the bulk content identifier and lists of locations where the content is stored. If not present at the user's location, the content is queued for transmission. Once at the user's location, the content is decrypted and format converted, if necessary, and transferred to the user over a LAN.

Further objects and advantages of the invention will become apparent from the description of preferred embodiments of the invention below.

BRIEF DESCRIPTION OF THE DRAWINGS

The present invention will now be described, by way of examples, with reference to the accompanying drawings, in which.

Throughout the drawing figures, like reference numerals will be understood to refer to like parts and components.

DETAILED DESCRIPTION OF PREFERRED EMBODIMENTS

Figure 1:
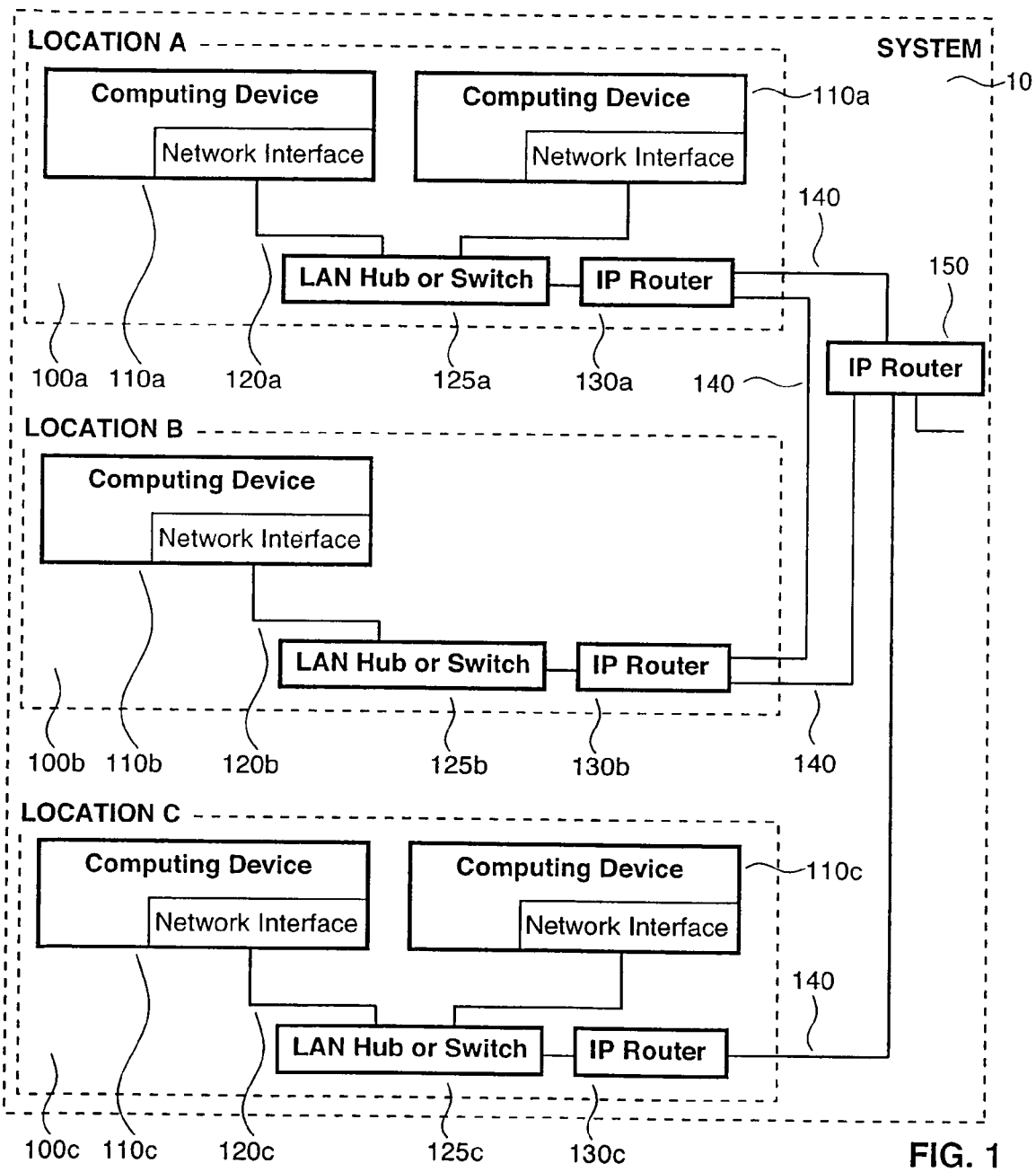
FIG. 1 is a schematic block diagram depicting the physical interconnection between computing devices in a medical data management system in accordance with an embodiment of the present invention.

A medical data management system 10 constructed in accordance with an embodiment of the present invention is depicted in FIG. 1, which is an example of the physical computing devices and the physical interconnection between them that comprise the system 10. A location 100, such as a hospital, clinic or medical laboratory, contains one or more computing devices 110, typically of the type known as a "server" to those skilled in the art, of which the ProLiant DL380, manufactured by the Hewlett Packard corporation, is an example. Such computing devices can contain a gigabyte of random access memory and a terabyte of disk storage at the present state of the art. One or more locations can also contain storage devices specialized for archiving to magnetic tape or optical media.

The computing devices at one location are connected to each other through Local Area Network (LAN) connections 120, comprised of commercially available hardware supporting a high-speed LAN protocol such as 10/100 BaseTX Ethernet, Gigabit Ethernet, Fiber Distributed Data Interface (FDDI), Asynchronous Transfer Mode (ATM) or Token Ring, which can include a LAN hub or switch 125.

The Local Area Network at a location also provides a connection to equipment that generates or displays medical data or which comprises an Electronic Patient Records (EPR) system or Hospital Information System (HIS) that manages patient's appointments. Such equipment is not considered part of the apparatus of the invention and is not shown in FIG. 1.

A router 130 connects the LAN at a location to one or more Wide Area Network (WAN) interconnections 140 that provide data paths between locations. Such a WAN can be implemented by satellite or radio links or by running wires or fiber-optic cables but is usually provided by a third party, such as a telephone company. The WAN can contain many devices hidden within it, such as routers 150 or frame-relay switches, that bridge interconnections. These remote devices are of interest because they will discard data when fed a higher rate of data from one interconnection than they can transmit on another, a situation that can easily arise when a hospital with a high-speed WAN interconnection sends data to a hospital with a lower-speed WAN interconnection.

When the WAN is provided by a third party, an inexpensive and common configuration comprises a single interconnection to each location. The interconnections support a lower data bandwidth than the "backbone" paths within the WAN. Several of the embodiments of the present invention provide improved performance for this type of configuration because the single interconnection to each location can be considered the only bottleneck.

It will be appreciated by those skilled in the art that routers which support the Internet Protocol (IP) are preferably the most common and inexpensive implementation; however, other WAN protocols, such as frame relay, Data Over Cable Service Interface Specification (DOCSIS), Asymmetrical Digital Subscriber Line (ADSL), Integrated Services Digital Network (ISDN), Digital Signal Services (e.g., DS1), Synchronous Optical Network (Sonet) or Asynchronous Transfer Mode (ATM) can be used, alone or in combination with IP or each other, as local pricing and availability dictates.

The computing devices 110 execute a multiprocessing operating system, which is Linux in the preferred embodiment but which could be others, such as those commonly known as Unix, Solaris, VXWorks, OS X and Windows or any other that supports multiprocessing, network protocols and LAN interfaces.

Figure 2:
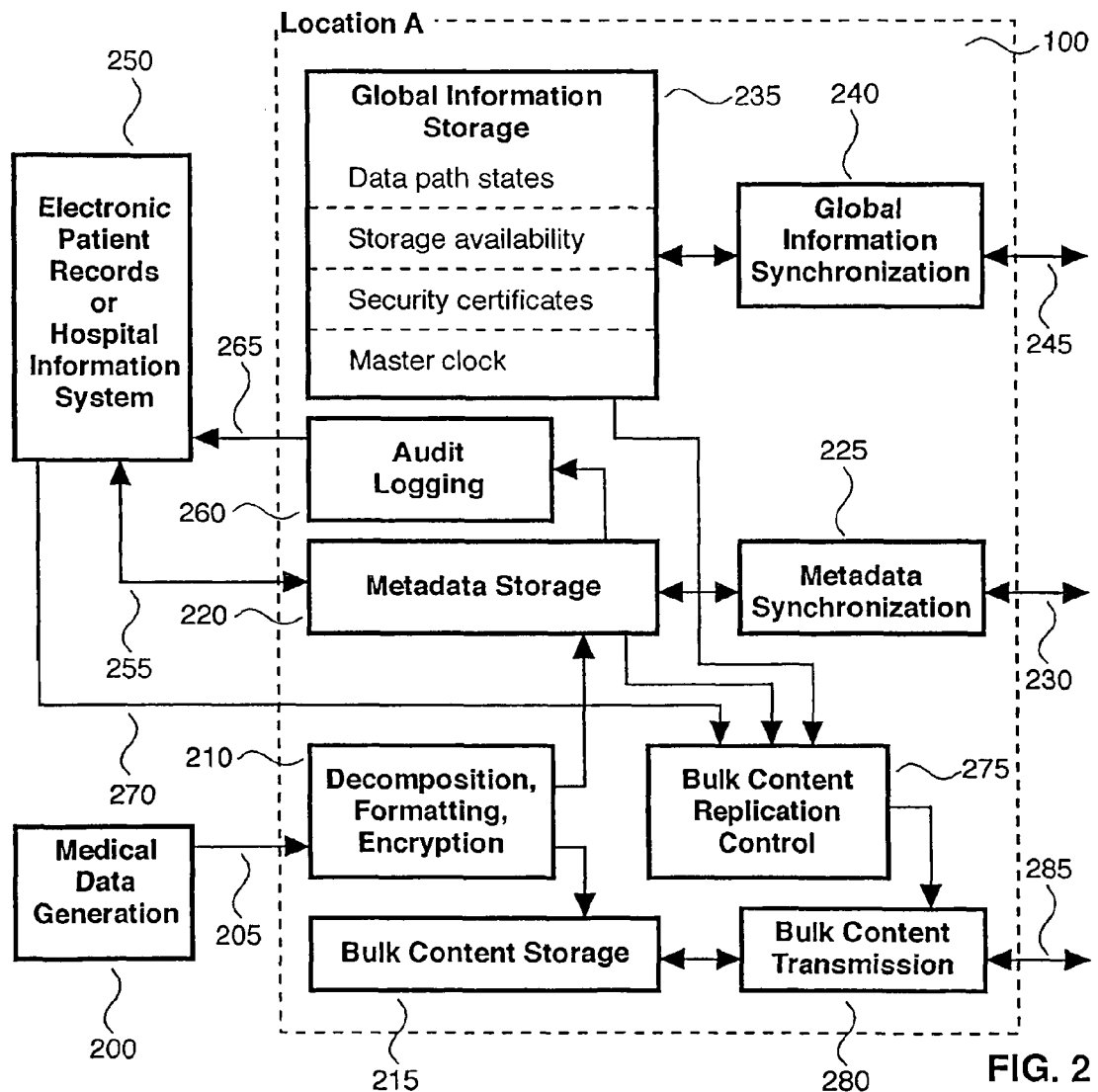
FIG. 2 is a schematic block diagram depicting the processing functions and major logical connections of devices a medical data management system in accordance with an embodiment of the present invention.

FIG. 2 shows the processing functions at the locations 100, which execute under control of the multiprocessing operating system or systems at each location in order to perform the method of the present invention. In the preferred embodiment, these functions are implemented as processes which can be installed in any or all computing devices 110 at a location 100. In a typical configuration of the preferred embodiment, when several computing devices are at a single location, the bulk content storage and transmission functions, 215 and 280, are installed in all computing devices to provide large storage capacity, while the other storage, control and transmission functions (220, 225, 235, 240 and 270) are installed in only one computing device per location. Typically, interface functions (such as 210 and 260) are installed only when required to connect to external devices.

It should be noted that the connections between the processing functions shown in FIG. 2 are logical; that is, the functions are not directly connected but instead use the operating system to transmit messages (e.g., known as Application Protocol Data Units or APDUs) over the Internet Protocol (or other protocols) supported by the hardware as described in the discussion of FIG. 1.

A medical data generation function 200, typically located inside an imaging device such as a computed tomography machine, transfers medical data to the invention via a logical connection 205 (over the LAN), implemented in the preferred embodiment by any of a variety of standard protocols such as DICOM, ANALYZE, Health Level 7 (HL7) and manufacturer-specific protocols such as those provided by some General Electric equipment. Such protocols usually transmit the name of the patient and other relatively brief information (collectively referred to herein as metadata) which describes the bulk content. The content itself generally consists of one or more images totaling as much as four gigabytes in size at the present state of the art.

Decomposition function 210 separates the metadata from the bulk content. It can convert some types of content to a standard format and compress or decompress it. It can also encrypt the content before passing it to a bulk storage function 215 for storage on disk. It can also add items to the metadata such as the time of arrival of the medical data, a cryptographic checksum (hash) of the bulk content and an identifier for the content. In the preferred embodiment, the identifier is a 64-bit random integer; however, alternative embodiments can use an integer chosen sequentially from a range of available values, a checksum of the content or an integer or string obtained from the metadata.

Decomposition function 210 also adds to the metadata a list of locations at which the associated bulk content is stored (initially, just one). In the preferred embodiment, the list consists of IP addresses of the computing devices storing the bulk content, from which the locations can be derived. In other embodiments, the list can comprise the identifiers of the actual locations, such as hospitals and clinics.

The decomposition function 210 passes the extended metadata to a metadata storage function 220 for storage on disk. In the preferred embodiment, the actual storage is performed by commercial database software, such as the Oracle9i database product manufactured by Oracle Corporation.

To provide reliability and to allow users to rapidly determine what medical data is available and where it is located, the metadata must be widely distributed, typically to each location where access is allowed. A metadata synchronization function 225 initiates logical connections with other locations to perform this service. In the preferred embodiment, each synchronization function periodically initiates a connection 230 to one of several others, over which information is exchanged. The list of connections, which specifies the topology for synchronization, is obtained from the global information storage function 235. Typically, the topology will be a spanning tree with added redundancy, manually defined when the invention is installed.

Because the metadata synchronization in the preferred embodiment is performed by connections between pairs of synchronization functions, the known "Bayou anti-entropy" method is preferably used to ensure that the stored information stabilizes correctly. This method requires changes to the metadata to be time-stamped in a change log and an exchange of version vectors between connected synchronization functions. In an alternative embodiment, changes to the metadata are broadcast throughout the network, either periodically, or as changes occur, or both.

Global information storage function 235 keeps the current network configuration and state information. Such information can include the network topology, transmission costs, state of the network's data paths and equipment, the amount of free storage at each location, encryption keys for stored data and security certificates used to authenticate network connections.

The global storage function 235 can also support a master clock so that accurate time is be available for audit logs, security certificate validation, and metadata change log timestamps. For some embodiments, the time can be obtained from a network-connected time server using the known Network Time Protocol. Other embodiments can use a Global Position System, cellular telephony Code Division Multiple Access (CDMA) or WWVB radio receiver to obtain the correct time, examples of which are the GPS-PCI2 receiver manufactured by the Symmetricom, Inc. and the TSAT-PCI receiver manufactured by the KSI division of DSPCon, Inc.

Global information synchronization function 240 initiates logical connections with other locations to synchronize the slowly changing global data. In the preferred embodiment, each synchronization function periodically initiates a connection 245 to one of several others, over which information is exchanged, using the same method of synchronization that was described for metadata. In an alternative embodiment, changes to the global data are broadcast throughout the network, either periodically or as changes occur, or both.

Electronic Patient Records (EPR) system or Hospital Information System (HIS) 250 connects to the computing device(s) 110 at the location(s) 100 of the medical data management system 10 of the present invention with logical connection 255 (over the LAN) to query metadata, and inform the location(s) 100 in the system 10 of upcoming appointments or other uses of the bulk content.

Audit logging function 260, which can be present at some locations 100, formats logging information stored with the metadata, transmitting the logging information to an Electronic Patient Records system or Hospital Information System via logical connection 265 (over the LAN). To assist in protecting patient privacy, the logging information preferably consists of a record for each access to metadata and bulk content which, at minimum, contains a description of the operation performed, a user identifier and a time stamp.

Bulk content replication control function 270 copies bulk content to other location via logical connection 285. The optimal locations to which to copy the bulk content are calculated based on a variety of information maintained by the global information storage function 235 and metadata storage function 220. In accordance with the preferred embodiment, the computing device(s) 110 at each location 100 in the system 10 obtains the desired degree of content duplication from the global information. The computing devices(s) 110 also ranks locations based on the following items of global information: available storage at each location, geographic distance to each location, transmission cost to each location, current utilization of the data paths to each location and processor utilization at each location. The computing device (s) 110 also uses the following items in the bulk content's associated metadata to rank locations: information that might indicate a location at which it will be accessed, such as the referring doctor or the doctor's clinic identifier, requests to use and prior usage of the bulk content and upcoming appointments or other future uses of the bulk content scheduled by the Electronic Patient Records (EPR) system or Hospital Information System (HIS) 250. In an alternative embodiment, the bulk content replication control function 270 also uses an estimate of the data path bandwidth to each location to rank locations.

In accordance with a preferred embodiment, the ranking of locations is facilitated by providing a simple programming language with which is manually defined a comparison function that calculates the relative ranking of any two locations using the items of global information and metadata. In another embodiment, a weighted sum is used to calculate a score for each location by which the locations are ranked. The weights, which are manually entered, are multiplied by values extracted from the items of global information and metadata.

In accordance with a preferred embodiment, one or more of the computing devices 110 at each location 100 estimates transmission costs with a manually-entered table maintained by the global information storage function 235. Each location is assigned a group identifier, and the table is a rectangular matrix that estimates the transmission costs from one location group to another. In another embodiment, groups are not used. The table instead indicates the cost from one location to another. In a third embodiment, the table changes dynamically to reflect the current cost of transmission for Wide Area Networks provided by carriers that charge for transmission based on the amount of usage, such as a surcharge for usage above a specified limit.

Over time, in accordance with a preferred embodiment of the present invention, bulk content replication control function 270 continues to recalculate optimal locations for storage of the bulk content as events occur such as requests to use the bulk content, new appointments, data path failures or equipment failures. As a result of the calculation, additional copies are made by transmitting content with a calculated priority, or copies are deleted. For example, each location can determine the optimal locations for bulk content storage and delete selected content stored at that location as needed based on this determination. Alternatively, the location where the content originated or the destination location (e.g., the clinic from which a doctor ordered a set of x-rays) can send messages to other locations to delete the content. When such changes are made, the metadata is updated with a new list of locations for the content.

Bulk content replication control function 270 copies bulk content by requesting bulk content transmission function 280 to send data over logical connection 285 to another location. In one embodiment, the transmission function opens a connection to transmit each bulk content using the known Transmission Control Protocol (TCP), relying on TCP congestion control mechanisms (e.g., slow start, exponential backoff and round-trip-time variance estimation) to deliver the content regardless of path bandwidth and to fairly share the path between competing transmissions.

In another embodiment, transmissions of the bulk content to the optimal locations are queued based on a priority calculated from the following items in the bulk content's associated metadata: information that might indicate urgency, such as an "urgent" or "abnormal" flag, requests to use and prior usage of the bulk content and upcoming appointments or other future uses of the bulk content scheduled by the Electronic Patient Records (EPR) system or Hospital Information System (HIS) 250. The transmission function opens a connection to transmit each bulk content using the known Transmission Control Protocol (TCP) or, in an alternative embodiment, sends sequential pieces of each bulk content using the known User Datagram Protocol (UDP).

The queue based on priority is implemented by having, at each location 100, a processing function that maintains the current priority of transmission. Bulk content transmission function 280 periodically checks the current priority and pauses transmission of any bulk content of lower priority. In another embodiment, the priority is checked each time a specified number of bytes are transmitted. In a third embodiment, a priority level for reception is also maintained at each location, and a sender must check both the local transmission priority and the receiving location's reception priority while transmitting bulk content.

FIG. 2 does not show function associated with bulk content retrieval, which is the reverse of decomposition function 210. When data is to be obtained by a user, the metadata at the user's location or a nearby location is searched to obtain the bulk content identifier and lists of locations where the content is stored. If not present at the user's location, the content is queued for transmission. Once at the user's location, the content is decrypted and format converted, if necessary, and transferred to the user over a LAN.

Figure 3:
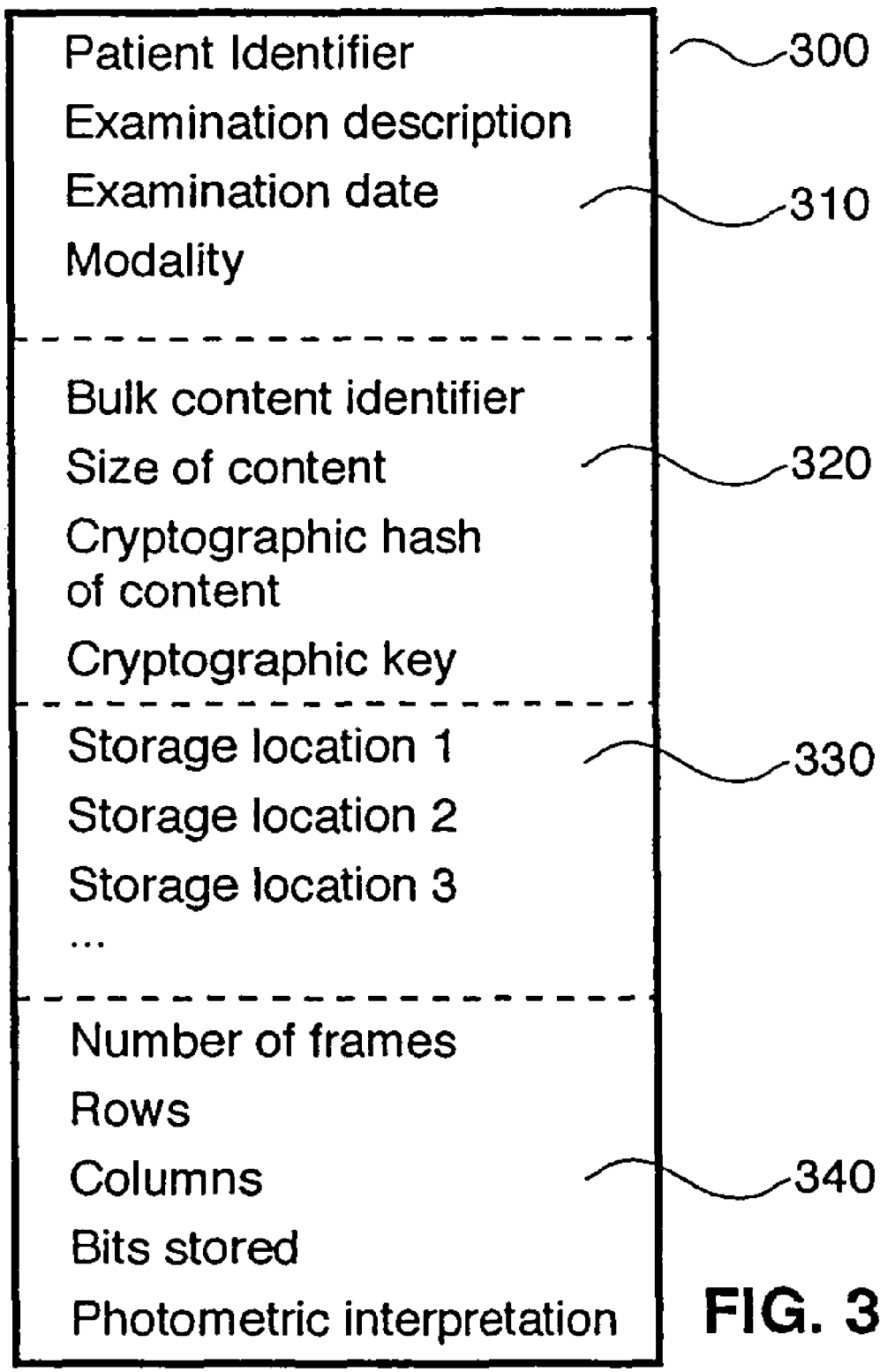
FIG. 3 illustrates an example of metadata employed in a medical data management system in accordance with an embodiment of the present invention.

FIG. 3 shows a simplified example of metadata 300 whereby some of the detailed information has been omitted for clarity. For explanatory purposes, the metadata is divided into four groups. Group 310 comprises of information about the patient and examination that can be used as a key to search the metadata storage. Group 320 comprises of information used within the system 10 for administrative and security purposes. Group 330 comprises a list of locations where the associated bulk content can be found. Group 340 comprises details about the bulk content that is useful when the content is viewed. In one embodiment, these groups could be stored together. In another embodiment, one or more groups of metadata can be in separate database tables as convenience dictates.

Figure 4A:
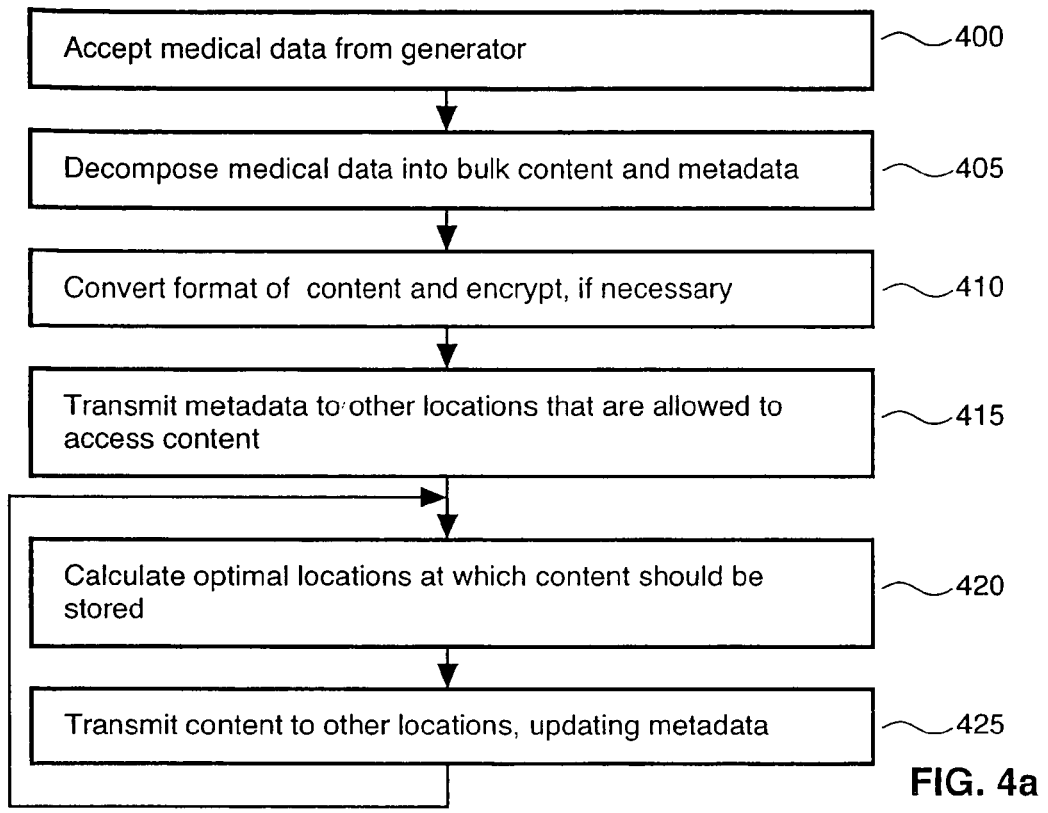
FIGS. 4A and 4B are flow charts depicting a sequence of operations for medical data storage and retrieval in accordance with an embodiment of the present invention.
Figure 4B:
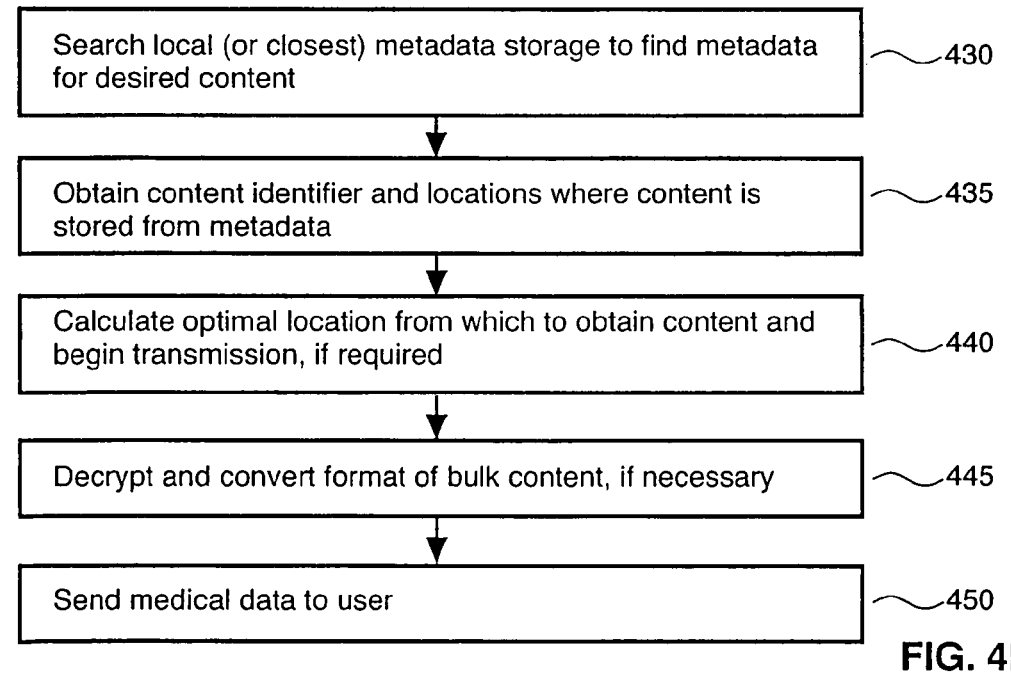

FIGS. 4A and 4B show the phases of medical data storage and retrieval, respectively. In step 400, 405 and 410, decomposition function 210 accepts medical data from the generating equipment, decomposes it into bulk content and metadata and converts its format and encrypts it, if necessary. In step 415, metadata synchronization function 225 transmits the metadata to several other locations which then continue to transmit the metadata until all locations 100 that are allowed to access it have been reached. In step 420, bulk content replication control function 275 calculates the optimal locations at which the bulk content should be located, as previously described. In step 425, bulk content transmission function 280 transmits the bulk content, in some embodiments queue by priority, as previously described.

For data retrieval, in step 430, metadata storage function 220 searches for the desired metadata records, based on a user request. In step 435, the content identifier is extracted from the metadata. In step 440, the optimal location from which to obtain the content is determined by the bulk content replication control function 275 and bulk content transmission function 280 begins transmission, in some embodiments queued by a priority that reflects the request. In step 445, the bulk content is decrypted and format converted, if necessary, and combined with metadata by a composition function that is the reverse of decomposition function 210. In step 450, the composition function sends the data to the user over the LAN.

A system incorporating the method and apparatus of the present invention is completely distributed and carefully manages the transmission between its locations. The capital cost of its equipment is distributed among its locations based on usage rather than centralized, which can be an advantage to some purchasers.

Thus, the system of the present invention provides for reliable, private, decentralized storage and rapid retrieval of medical data amongst geographically separate locations, connected by data paths of limited bandwidth, and optimizes the transmission between the locations. New medical data arriving is separated into bulk content and metadata. The metadata is transmitted, generally to all locations. The optimal locations to which to copy the bulk content are calculated based on the desired duplication, available storage, geographic distance, transmission cost, data path bandwidth, data path utilization, processor utilization or likelihood of retrieval calculated from the metadata, from requests to use or prior usage of the content or from information obtained from a system that manages future uses of the content. To avoid overloading the data paths, the transmission rate is limited and the bulk content is queued for transmission based on a priority calculated from the metadata, from requests to use the content or from information obtained from a system that manages future uses of the content. Over time, the optimal locations for the bulk content are recalculated as events such as requests to use the content, new patient appointments, data path failures or equipment failures occur. Additional copies are made or copies are deleted and distributed lists of locations for the content are updated.

While only preferred embodiments of the invention have been described herein in detail, the invention is not limited thereby and modifications can be made within the scope of the attached claims.

What is claimed is:

1. A method for transmission of digital data between at least two separate locations, the method comprising:
   separating the data arriving at one of the locations into at least bulk content and metadata;
   selecting one or more target locations from the locations for storage based on a calculation using storage capacity available at respective ones of the target locations, processor utilization available at respective ones of the target locations, and network bandwidth available to respective ones of the target locations, the calculation transforming values relating to the storage capacity, the processing utilization and the network bandwidth associated with the target locations into rankings of the target locations with respect to each other;
   transmitting the bulk content to at least one of the selected target locations; and
   storing the bulk content at the at least one of the selected target location %
   wherein, when the bulk content has been stored at the selected target locations and an event occurs that changes the rankings of the locations, the method further comprises determining that the rankings of one or more locations have changed; and
   recalculating the rankings of the locations.

2. A method as claimed in claim 1, wherein the metadata separated from the bulk content is also used in the calculation of the selected target locations for where to transmit the bulk content.

3. A method as claimed in claim 2, wherein information from at least one of an external database and an information system comprising one of an Electronic Patient Record and a Hospital Information System is also used in the calculation of the selected target locations for where to transmit the bulk content.

4. A method as claimed in claim 1, wherein the calculation used in selecting the target locations is based on a series of formulas that incorporate weighted sums and products to use weightings to transform the values relating to the storage capacity, the processing utilization and the network bandwidth associated with the target locations into a ranking of the target locations with respect to each other.

5. A method as claimed in claim 4, wherein the weightings used to calculate the rankings of the target locations are configurable on a location-by-location basis and can change over time.

6. A method as claimed in claim 1, wherein one or more selected target locations are not currently available, the method comprising:
   determining that one or more selected target locations are not available due to at least one of data path failure and equipment failure;
   queuing the bulk content for transmission;
   storing the bulk content until the selected locations become available;
   transmitting the bulk content to at least one of the selected locations and storing it.

7. A method as claimed in claim 6, further comprising re-calculating the rankings of the storage locations when the selected target locations become available and before transmitting the bulk content.

8. A method as claimed in claim 6, wherein the priority and order of the transmission of the queued bulk content is based on the metadata separated from the bulk content.

9. A method as claimed in claim 1, wherein one or more selected target locations are not optimal, the method comprising:
   determining that one or more selected target locations are not optimal due to at least one of data path failure, equipment failure, historical usage and predicted usage; and
   queuing the bulk content for transmission.

10. A method as claimed in claim 9, further comprising re-calculating the rankings of the storage locations before transmitting the bulk content to at least one of the selected locations for storage.

11. A method as claimed in claim 9, wherein the priority and order of the transmission of the queued bulk content is based on the metadata separated from the bulk content.

12. A method as claimed in claim 1, wherein one or more selected target locations are not optimal, the method comprising:
   determining that one or more selected target locations are not optimal due to at least one of data path failure and equipment failure, historical or predicted usage;
   deleting the bulk content from at least one of the selected locations.

13. A method as claimed in claim 1, wherein
   the recalculating comprises: determining a new set of selected target locations; and
   selectively transmitting the bulk content to at least one of these newly selected target locations and storing it if the newly selected target location is higher ranked or not already one of the selected target locations.

14. A method as claimed in claim 13, wherein when the bulk data stored on the originally selected target locations is removed after being transmitted and stored to the newly selected target locations.

15. A method as claimed in claim 13, wherein the metadata separated from the bulk content is also used in the re-calculation of the selected target locations for where to transmit the bulk content.

16. A method as claimed in claim 15, wherein at least one of information from an external database and an information system comprising at least one of a Electronic Patient Record and a Hospital Information System is also used in the re-calculation of the selected target locations for where to transmit the bulk content.

17. An apparatus for transmission of digital data between at least two separate locations connected by optical, wired or radio frequency data paths of limited bandwidth, the apparatus employed at a first one of the locations and comprising:
   a processing device;
   a memory device coupled to the processing device; and
   at least one network interface connected to at least one of the data paths and in communication with the processing device;
   wherein the processing device is programmed to separate the data arriving at one of the locations into at least bulk content and metadata, select one or more target locations from the locations for storage based on a calculation using storage capacity available at respective ones of the target locations, processor utilization available at respective ones of the target locations, and network bandwidth available to respective ones of the target locations, and transmit the bulk content to at least one of the selected target locations for storage, the calculation transforming values relating to the storage capacity, the processing utilization and the network bandwidth associated with the target locations into rankings of the target locations with respect to each other; and
   wherein, when the bulk content has been stored at the selected target locations and an event occurs that changes the rankings of the locations, the processor is programmed to determine that the rankings of one or more locations have changed, and recalculate the rankings of the locations.

18. An apparatus as claimed in claim 17, wherein one or more selected target locations are not currently available, the processing device being programmed to determine that one or more selected target locations are not available due to at least one of data path failure and equipment failure, queue the bulk content for transmission, store the bulk content in at least one of the memory device and another memory device until the selected locations become available, and transmit the bulk content to at least one of the selected locations for storage when it becomes available.

19. An apparatus as claimed in claim 17, wherein one or more selected target locations are not optimal, the processing device being programmed to determine that one or more selected target locations are not optimal due to at least one of data path failure, equipment failure, historical usage and predicted usage, and queue the bulk content for transmission.

20. A method as claimed in claim 19, wherein recalculating the rankings of the storage locations comprises determining a new set of selected target locations, the processing device being programmed to selectively transmit the bulk content to at least one of the newly selected locations for storage if the newly selected target location is higher ranked or not already one of the selected target locations.

* * * * *

UNITED STATES PATENT AND TRADEMARK OFFICE
CERTIFICATE OF CORRECTION

| | | |
|---|---|---|
| PATENT NO. | : 7,925,759 B2 | Page 1 of 1 |
| APPLICATION NO. | : 12/216282 | |
| DATED | : April 12, 2011 | |
| INVENTOR(S) | : David Slik et al. | |

It is certified that error appears in the above-identified patent and that said Letters Patent is hereby corrected as shown below:

In the Claims:

In column 10, line 25 in claim 1, delete "%" and insert --;--, therefor

Signed and Sealed this
Seventeenth Day of September, 2013

Teresa Stanek Rea
*Deputy Director of the United States Patent and Trademark Office*